United States Patent [19]

Jacobs et al.

[11] Patent Number: 4,935,374
[45] Date of Patent: Jun. 19, 1990

[54] POLYETHYLENE EVAPORATION COVERS

[75] Inventors: Merrit N. Jacobs, Fairport; Catherine S. Przybylowicz, Rochester, both of N.Y.

[73] Assignee: Eastman Kodak Company, Rochester, N.Y.

[21] Appl. No.: 346,206

[22] Filed: May 2, 1989

[51] Int. Cl.$^5$ .......................................... G01N 33/00
[52] U.S. Cl. ................................. 436/103; 436/165; 422/63; 422/99; 422/102; 422/104; 350/534; 350/536
[58] Field of Search .................. 436/103, 165; 422/99, 422/104, 65, 68, 102; 350/534, 536

[56] References Cited

U.S. PATENT DOCUMENTS 4,258,001  3/1981  Pierce et al. .......................... 422/56
4,777,020  10/1988  Brigati ................................. 422/99

FOREIGN PATENT DOCUMENTS 0191650  2/1986  European Pat. Off.
63-47661  2/1988  Japan.

Primary Examiner—Robert J. Warden
Assistant Examiner—Lynn M. Kummert
Attorney, Agent, or Firm—Dana M. Schmidt

[57] ABSTRACT

There are disclosed polyethylene evaporation covers and a method of analysis that uniquely solve the problem of contamination of CKMB test elements when phosphorous test elements are incubated in the same incubator. The solution is to have the surface of the evaporation cover the contacts the test element, be non-porous polyethylene.

2 Claims, 1 Drawing Sheet

POLYETHYLENE EVAPORATION COVERS

FIELD OF THE INVENTION

This invention relates to incubators used in clincial analyzers and specifically to the evaporation covers for such incubators.

BACKGROUND OF THE INVENTION

Analyzers using the so-called dried test elements in which the reagents are pre-incorporated in a dried format, have allowed a large number of different tests to be conducted. These include slide-like test elements that react colorimetrically to assay, for example, for phosphorous and CKMB. In the past, phosphorous tests have been incubated in end-point incubators, along with other end-point assays, while CKMB has been incubated in a separate rate-assay incubator.

To simplify the analyzer, there has been a need to make one incubator, hereinafter "single incubator", function for both rate and end-point assays. However, there has been a problem prior to this invention when phosphorous test elements have been incubated together with CKMB test elements. For reasons which were not clear, if phosphorous had been tested at an incubator station prior to a CKMB test element, the latter produced a higher reading than it should have. Although the operator could endeavor to run CKMB tests at a totally different time than phosphorous tests, this is an unacceptable limitation for most laboratories, particularly those involved in STAT operations, that is, those that must be run immediately.

Yet another problem encountered by certain test elements is that their detected levels of analytes have been routinely higher when tested on this single incubator, than expected, particularly when compared to the reading obtained on a dedicated colorimetric analyzer. These are elements in which the spreading layer first contacted by the sample is a beaded spreading layer of the type described in U.S. Pat. No. 4,258,001, particularly useful in assays such as total protein and albumin. Again, the cause of this positive bias has not been clear prior to this invention. It will be understood that such bias could be acceptable if the math modeling were adjusted to correct for the bias (when providing the conversion of reflectance to concentration.) However, in switching to a single incubator for both rate and colorimetric assays, it is preferred that as much of the software used in the conventional colorimetric analyzers and rate analyzers, be adapted or transferred to the single incubator, as possible. Since the bias present, e.g., in total protein takes the values completely out of the "normal" reading domain heretofore used, such transfer heretofore has not been possible.

Japanese Kokai No. 63/47661 published Feb. 29, 1988 teaches the use of a wide variety of non-porous, non-absorbing polymers for evaporation covers at incubator stations featuring dried test elements. The polymers listed as being useful are polyolefins such as polyethylene and polypropylene, polyesters such as polyethylene terephthalate, butylene terephthalate and polyethylene-polybutylene terephthalate. The purpose is stated to be to reduce the absorption of any reactive gas produced by a test element. However, the only reactive gas that is specifically discussed is ammonia from BUN test elements. There is no appreciation of the cause of the problem created when one incubator has to be used for both phosphorous test elements and CKMB test elements. There is, furthermore, no discussion of a colorant to be used in the cover, or of problems associated with test elements constructed using beaded spreading layers.

SUMMARY OF THE INVENTION

I have discovered the causes of the above-noted problems. In the case of the CKMB bias, it is that $SO_2$ gas produced by the phosphorous test elements as a by-product, is an interferant in the CKMB reaction and will carry-over in amounts that can affect a subsequent CKMB test element. I have solved this problem by determining that only polyethylene has superior resistance to the $SO_2$ carry-over. As to the bias occurring with beaded spreading layer elements, that is caused by their translucency, and the passage of detecting light out of the elements so as to reflect off a heretofore non-white evaporation cover used in the single incubator.

More particularly, in accord with one aspect of the invention, there is provided a single incubator in which both phosphorous and CKMB tests are run using dried test elements, the incubator including (a) at least one station having both phosphorous and CKMB test elements therein at different times, the phosphorous test element being characterized by the production of $SO_2$ gas; (b) an evaporation cover at the station for covering the top of a porous test element at the station; and (c) means for detecting a colorimetric change in a test element while held at the station. The incubator is improved in that the evaporation cover comprises a surface material contacting the test element at the station that consists essentially of non-porous polyethylene, whereby carry-over of $SO_2$ gas from a phosphorous test to a CKMB test is significantly reduced.

In accord with another aspect of the invention, there is provided a method for preventing the biasing of a CKMB test element when incubated in the same incubator station previously occupied by a phosphorous test element, the station including an evaporation cover that covers the porous top of either the CKMB or phosphorous test elements, the method comprising the steps of incorporating into the incubator station as an exterior surface of the evaporation cover, a non-porous polyethylene, and reading said test element while in the incubator station, after a suitable period of incubation, whereby $SO_2$ gas produced by a phosphorous test element is not absorbed by said cover and is not carried over to a CKMB test element that occupies said station.

Accordingly, it is an advantageous feature of the invention that a single incubator can be used with both phosphorous and CKMB test elements without regard to the timing of those elements with respect to each other, and without the phosphorous test element contaminating the CKMB test element.

It is another advantageous feature of the invention that such an incubator can be used with test elements featuring beaded spreading layers without the development of a bias due to unwanted light absorption.

Other advantageous features will become apparent upon reference to the following description of the preferred embodiments when read in light of the attached drawing.

DESCRIPTION OF THE PREFERRED EMBODIMENTS

Figure 1:
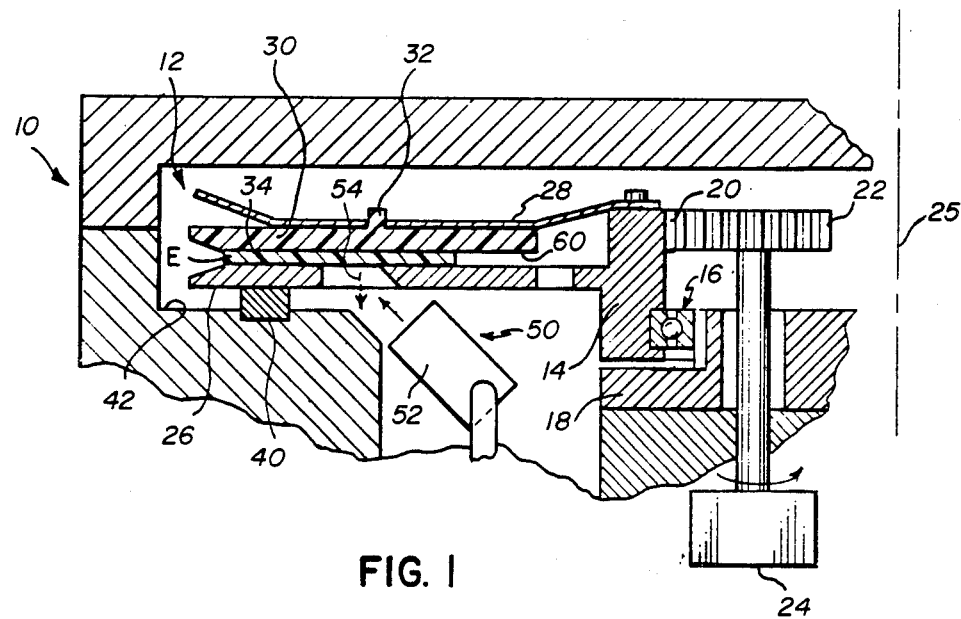
FIG. 1 is a fragmentary elevational view in section, of an incubator constructed in accordance with the invention.

The invention is discussed hereinafter in connection with preferred embodiments, that is, with an incubator of a particular construction, and with test elements such as those made under the trademark "Ektachem" by Eastman Kodak. In addition, the invention is useful in any incubator, and with dried test elements of other formats, provided that the incubator has both phosphorous and CKMB test elements run in it.

As will be seen by the following data, the presence of $SO_2$ gas, a by-product of the phosphorous test element, will reduce the reading that is the correct reading in a CKMB test element. As a result, unacceptable standard deviations of three or more, for an expected reading of 50, can occur. This is corrected by using as the evaporation cover, or at least the surface in contact with the porous top of the test elements that have received sample liquid, a polyethylene material. The polyethylene can be clear, or colored with any color or colored with a white pigment or dye for the reasons noted hereinafter, of sufficient density as to be non-porous to gas, for example, high-density polyethylene. The entire cover can be such polyethylene, or it can comprise a support material such as metal, bearing polyethylene on the exterior surface that contacts the test element.

In some cases, the test elements can have a translucent, beaded spreading layer as described in U.S. Pat. No. 4,258,001. Alternatively, a spreading layer can be used that is opaque, that is, incorporates a light-blocking agent. If the spreading layer is *not* opaque, we have discovered that the scanning light of the reflectometer at the reading station tends to penetrate beyond the test element, to be reflected off the evaporation cover. If, as has been customary in incubators other than those dedicated to colorimetric assays, such covers are of a material other than white, that light is reflected back with a spurious decrease in intensity, because of its partial absorption by the cover, even though there may be little or no dye produced by the assay in the element. When using such translucent spreading layers, the polyethylene cover preferably includes a white colorant, that is, a pigment, to prevent spurious absorption.

FIG. 1 illustrates a useful incubator 10, in which a plurality of stations 12 are mounted on a ring 14 journaled at 16 to a platform 18. Ring 14 can have gear teeth at 20 to engage a driving gear 22 operated by motor 24 to rotate the stations about axis 25. Each station 12 has a support plate 26 attached to ring 14, a spring 28 pressing down towards plate 26, and an evaporation cover 30 with a boss 32 projecting through the spring. A test element with a porous top surface 34, prewetted with liquid sample, is held between cover 30 and plate 26. Preferably, these height locating buttons 40 are spaced about stationary surface 42, one of which is adjacent read station 50, to insure that the proper vertical distance is maintained between element E and a light source 52 that is part of the read station. (A photodetector, not shown, is also present at the read station to receive reflected light, arrow 54.) Aperture 56 is provided in plate 26 to allow the reading of the element. This single incubator provides for the reading of both colorimetric and rate test elements, at read station 50.

In accordance with the invention, all, or at least the surface part 60, of cover 30 that contacts element E, is a polyethylene as described above. That polyethylene preferably includes a white colorant if the test elements E to be incubated and read are the type with a translucent beaded spreading layer.

EXAMPLES 1-4

To demonstrate the significance of the selection of polyethylene, and that it is unique as a material, four different batches of pooled human serum, all having a known CKMB activity of 50, were tested on "Ektachem" CKMB test elements using an incubator that had just prior to the CKMB test element, assayed for phosphorous using an "Ektachem" brand phosphorous test element. (The phosphorous test also used pooled human serum having the same amount of phosphorous in each case.) There were six incubator stations, and each was filled with the same kind of test element for each "fill". The results of the six stations were averaged and the standard deviation determined for n=6, for each "fill". The "fill" No. refers to the nth test element to be placed in that incubator station after the phosphorous test. That is, fill #1 was the 1st test element placed there, #2 the second, and so on. The results are listed in Table I.

TABLE I

| | Part A - Mean Concentrations (Units/l) | | | | |
|---|---|---|---|---|---|
| Fill No. | White Polyethylene | Natural (Colorless) Polyethylene | Poly-Propylene | Teflon | Metal |
| 1 | 47.329 | 46.391 | 43.196 | 40.195 | 41.326 |
| 2 | 49.474 | 49.98 | 48.945 | 47.744 | 46.913 |
| 3 | 49.159 | 50.569 | 50.156 | 49.984 | 52.311 |
| 4 | 49.931 | 50.736 | 50.55 | 54.104 | 53.509 |
| | Part B - Standard Deviations | | | | |
| Fill No. | White Polyethylene | Natural Polyethylene | Poly-Propylene | Teflon | Metal |
| 1 | 0.956 | 0.736 | 7.905 | 3.464 | 3.996 |
| 2 | 1.036 | 0.953 | 1.9 | 2.23 | 1.192 |
| 3 | 1.173 | 0.422 | 1.177 | 1.475 | 0.877 |
| 4 | 1.569 | 0.922 | 0.699 | 0.469 | 1.464 |

Two factors are important in this Table - the consistency from fill to fill in Part A, and the standard deviations of Part B. In the first of these, polyethylene was more consistent in its reading, ranging in the case of natural polyethylene from 46.391 to 50.736. Polypropylene on the other hand had a much bigger, and therefore unacceptable, range. This is supported by the second factor, the standard deviations. A standard deviation for polypropylene that is as high as 7.9 is totally unacceptable. On the whole, it was clear that polyethylene, with or without a colorant, was more likely to minimize error than any of the other materials (polypropylene, teflon or metal).

The invention has been described in detail with particular reference to preferred embodiments thereof, but it will be understood that variations and modifications can be effected within the spirit and scope of the invention.

What is claimed is:

1. A method for preventing the biasing of a CKMB test element incubated in the same incubator station previously occupied by a phosphorous test element, said station comprising a polyethylene evaporation cover that covers a porous top of either of said CKMB or said phosphorous test elements, the method comprising the steps of:

inserting a phosphorous test element into said same incubator station with patient sample thereon so that $SO_2$ gas is generated as a by-product at said station, reading said phosphorous test element and removing said phosphorous test element from said same station, thereafter inserting a CKMB test element into said same station and reading it, said polyethylene of said cover being effective to prevent $SO_2$ gas produced by said inserted phosphorous test element from being (a) absorbed by said cover and (b) carried over to said inserted CKMB test element.

2. A method as defined in claim 1, wherein said polyethylene includes a white colorant, to reflect any light that passes through a test element in said station without adding to the detected density of the test element.

* * * * *

UNITED STATES PATENT AND TRADEMARK OFFICE
CERTIFICATE OF CORRECTION

PATENT NO. : 4,935,374
DATED : June 19, 1990
INVENTOR(S) : Merrit N. Jacobs & Catherine S. Przybylowicz It is certified that error appears in the above-identified patent and that said Letters Patent is hereby corrected as shown below:

Face of Patent, ABSTRACT, line 6 should read:
--evaporation cover that contacts the test element, be--

Column 2, line 8 should read: --We have discovered the causes of the above-noted--

Column 2, line 13 should read: --CKMB test element. We have solved this problem by--

Column 3, line 61 should read: --Preferably, height locating buttons 40 are spaced--

Signed and Sealed this

Twenty-ninth Day of October, 1991

*Attest:*

HARRY F. MANBECK, JR.

*Attesting Officer*     *Commissioner of Patents and Trademarks*